United States Patent [19]

Akita

[11] 4,215,582
[45] Aug. 5, 1980

[54] ULTRASONIC TEMPERATURE MEASURING APPARATUS

[75] Inventor: Sigeyuki Akita, Aichi, Japan
[73] Assignee: Nippon Soken, Inc., Nishio, Japan
[21] Appl. No.: 12,134
[22] Filed: Feb. 14, 1979
[30] Foreign Application Priority Data Apr. 26, 1978 [JP] Japan .................................. 53-50371

[51] Int. Cl.² ...................... G01N 29/00; G01K 11/24
[52] U.S. Cl. ........................................ 73/579; 73/339 A
[58] Field of Search ............................... 73/597, 339 A

[56] References Cited

U.S. PATENT DOCUMENTS

| 3,320,808 | 5/1967 | Boyd et al. | 73/339 A |
| 3,620,070 | 11/1971 | Collins | 73/629 |
| 4,147,064 | 4/1979 | Bond | 73/597 X |

*Primary Examiner*—James J. Gill
*Attorney, Agent, or Firm*—Cushman, Darby & Cushman

[57] ABSTRACT

An ultrasonic temperature measuring apparatus includes a display section and a sensor section connected therebetween with a signal line and a ground line. The display section produces and transmits an excitation signal producing signal having a frequency 1/N times that of an excitation signal for a ultrasonic vibrator over the signal line to the sensor section. In the sensor section, in response to the excitation signal producing signal, the excitation signal is produced to excite the ultrasonic wave vibrator and to transmit the ultrasonic wave continuously into a propagation medium. The ultrasonic wave received at a receiver spaced from the ultrasonic vibrator by a predetermined distance is phase compared with the excitation signal and a pulse difference signal having a pulse width indicative of the phase difference and hence a temperature of the propagation medium is produced. The pulse width signal conveying temperature information of the medium is transmitted from the sensor section to the display section over the same signal line. The signal levels of the excitation signal producing signal and the temperature information signal are made different levels to distinguish from each other.

1 Claim, 10 Drawing Figures

ULTRASONIC TEMPERATURE MEASURING APPARATUS

BACKGROUND OF THE INVENTION

The present invention relates to apparatus for detecting the temperature of a medium of propagation such as air by a change in the velocity of propagation of ultrasonic wave due to the medium temperature, and more particularly the invention relates to an ultrasonic temperature measuring apparatus in which a temperature detecting sensor section and a temperature indicating display section are connected with each other by means of two electric wires.

SUMMARY OF THE INVENTION

It is the object of the present invention to provide an ultrasonic temperature measuring apparatus for measuring the temperature of an ultrasonic wave propagation medium. In accordance with the present invention, there is thus provided an ultrasonic temperature measuring apparatus comprising a display section and a sensor section whereby a signal of a frequency f which is one Nth of an exciting frequency for exciting an ultrasonic vibrator is superposed on an information signal and the information signal is then transmitted from the display section to the sensor section through a single signal line. In the sensor section, a power supply for supplying the various electronic circuits of the sensor section is produced from the received information signal, and the signal having the 1/N frequency f is read out from the information signal and increased by N times to produce an exciting signal having an exciting frequency N·f. Transmitting means is provided to respond to the exciting signal to generate an ultrasonic wave which in turn is received by receiving means, and the phase difference during a predetermined time interval between the pulse trains transmitted and received between the transmitting and receiving means is detected and superposed on the information signal which in turn is transmitted to the display section. Thus, it is possible to always transmit and receive ultrasonic waves continuously between the transmitting and receiving means and thereby to make stable temperature detection possible, and moreover the display section and the sensor section are connected with each other by two electric wires, i.e., a single signal line which serves as an information transmission line and a power supply line, and the other wire serves as a ground line.

Thus the apparatus of this invention has among its great advantages the fact that since the apparatus comprises two blocks, i.e., a sensor section and a display section whereby in the sensor section the transmision and reception of ultrasonic waves are effected continuously between transmitting and receiving means and the phase difference between the pulse trains transmitted and received between the transmitting and receiving means is detected in terms of a pulse width thus making it possible to stably detect a phase difference signal without being affected by, for example, the rising acteristics of the transmitting and receiving means and since, as regards the transmission and reception of signals between the display section and the sensor section, the display section is constructed so that a signal of a frequency f which is one Nth of the ultrasonic wave exciting frequency is superposed on an information signal which in turn is transmitted to the sensor section through a single signal line, the sensor section is constructed so that the signal of the frequency f and a predetermined power supply are derived from the information signal and the display section is also designed so that the phase difference signal from the sensor section is read out to determine and display the temperature of a medium between the transmitting and receiving means in accordance with the pulse width of the phase difference signal, it is possible to stably detect the temperature of the medium and moreover it is possible to connect the display section and the sensor section by only two electric wires, i.e., the single signal line serving as the information transmission line as well as the power supply line and the ground wire.

DESCRIPTION OF THE PREFERRED EMBODIMENT

Figure 1:
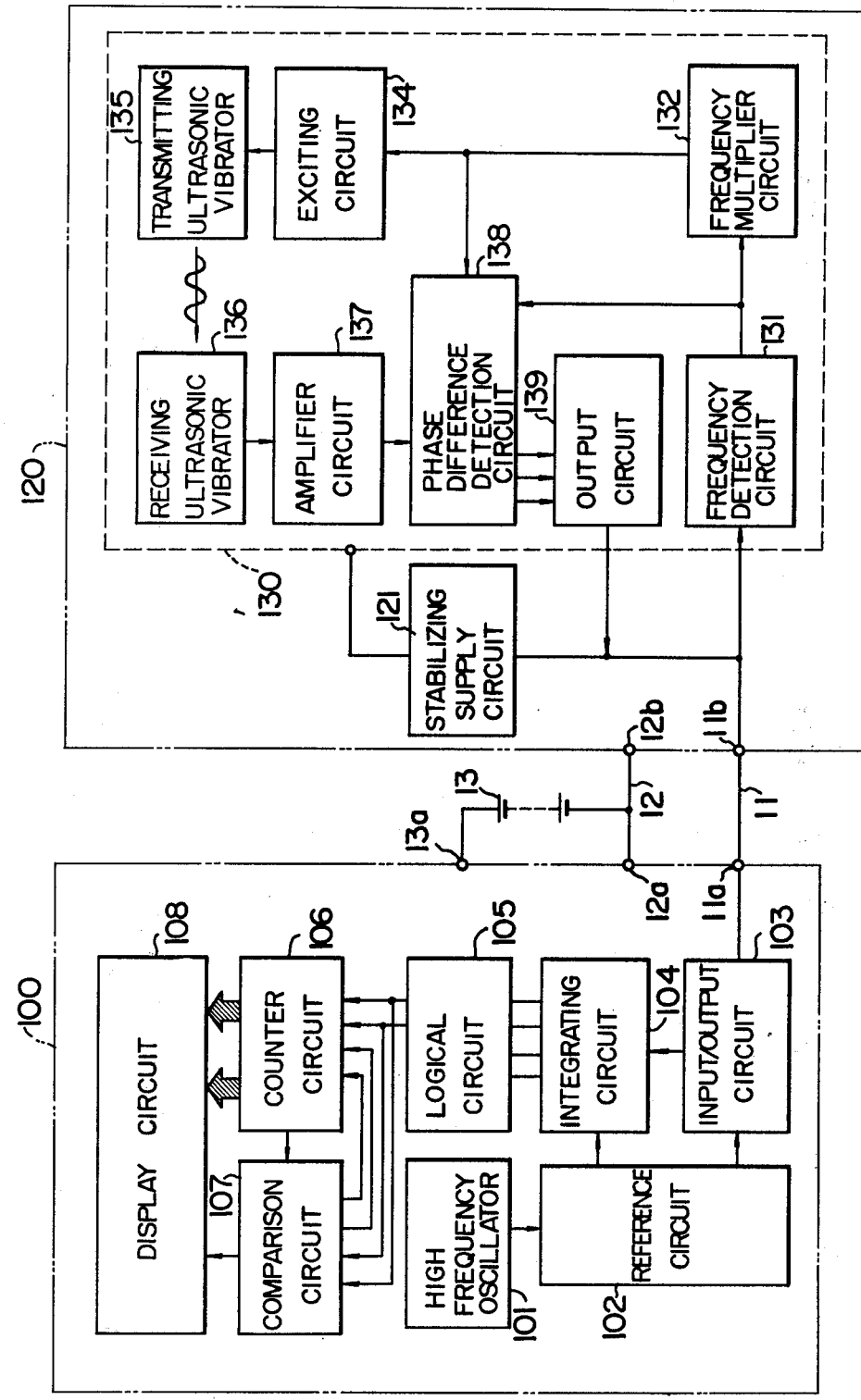
FIG. 1 is a block diagram showing an overall general construction of an embodiment of an ultrasonic temperature measuring apparatus according to the invention.

The present invention will now be described with reference to the illustrated embodiment. Referring first to the block diagram of FIG. 1 showing the overall construction of the embodiment, block 100 designates a display section and block 120 designates a sensor section. The display section 100 and the sensor section 120 are connected to each other by a single signal line 11 and a ground wire 12, and the signal line 11 serves the function of signal transmission and the function of supplying power to the sensor section.

Referring now to the display section 100, numeral 101 designates a high frequency oscillator comprising a crystal vibrator or the like and adapted to oscillate at a predetermined frequency stably in temperature, 102 a reference circuit for producing from the high frequency oscillation frequency a signal of a frequency which is one Nth of an excitating frequency for exciting a transmitting ultrasonic vibrator in the sensor section, 103 an input/output circuit for delivering the 1/N frequency signal to the sensor section 120 and also for receiving a temperature detection signal from the sensor section 120, 104 an integrating circuit for integrating a temperature detection signal, 105 a logic circuit for producing a storage signal and a reset signal, 106 a counter circuit for counting the integrated signal from the integrating circuit 104, 107 a comparison circuit for determining whether the temperature of air is positive or negative, and 108 and a display circuit or unit for displaying the temperature of air.

In the sensor section 120, numeral 121 designates a stabilizing supply circuit for producing a power supply for a sensor proper 130 from the signal supplied through the signal line 11, 131 a frequency detection circuit for detecting the signal of a frequency which is one Nth of the exciting frequency from the signal line 11, 132 a frequency multiplier circuit for producing an exciting frequency which is N times that of the 1/N signal, 134 an excitation circuit for exciting an ultrasonic vibrator, 135 a transmitter comprising a transmitting ultrasonic vibrator such as a piezoelectric element, 136 a receiver comprising a receiving ultrasonic vibrator for always receiving the exciting frequency, 137 an amplifier circuit for amplifying a received signal, 138 a phase difference detection circuit for detecting the phase difference between the pulse trains of the transmitted and received signals, and 139 an output circuit for superposing on the line 11 a phase difference signal of a time width corresponding to the temperature of the medium.

Figure 2:
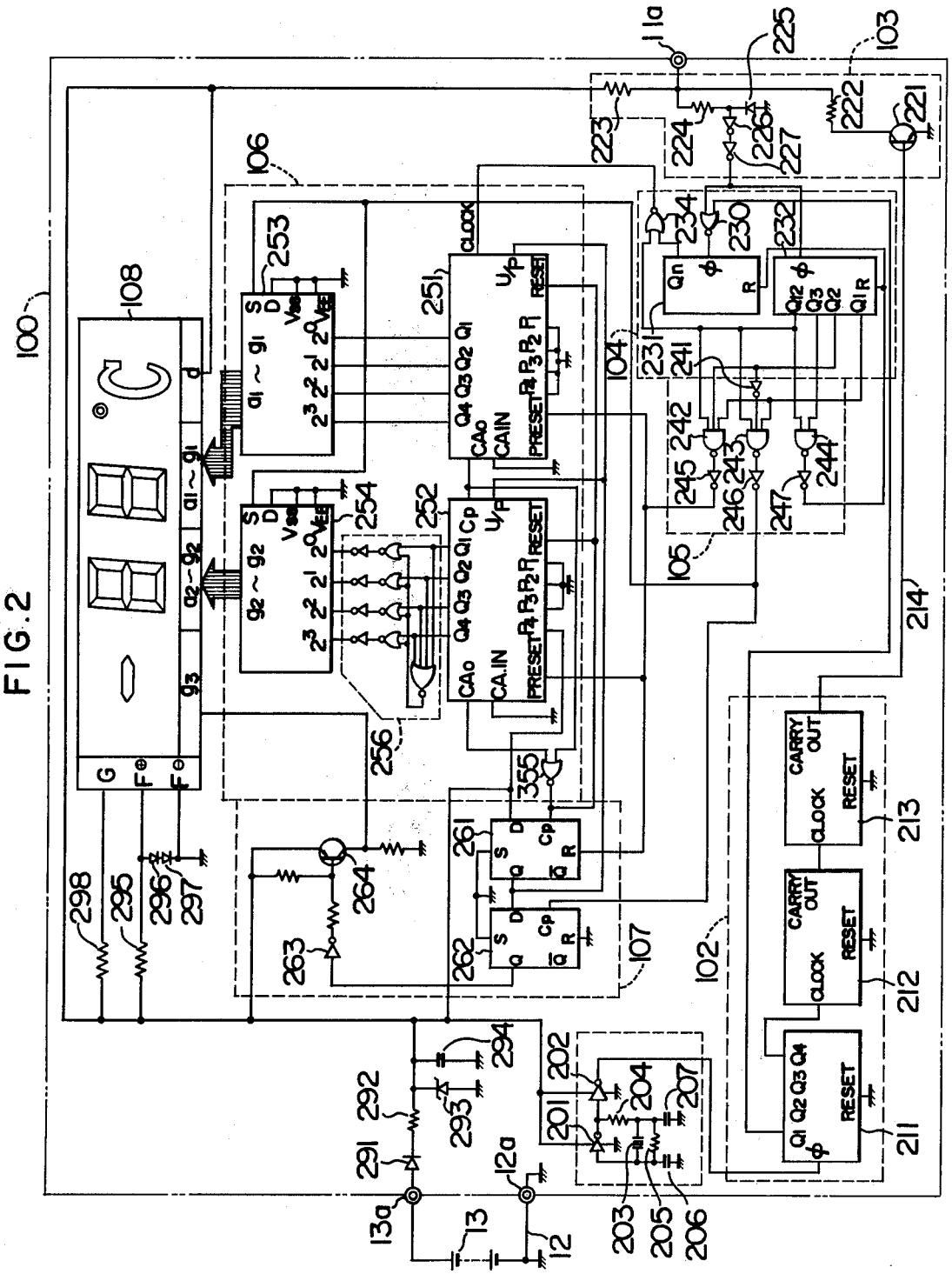
FIG. 2 is a wiring diagram showing a detailed circuit of the display section shown in FIG. 1.
Figure 3:
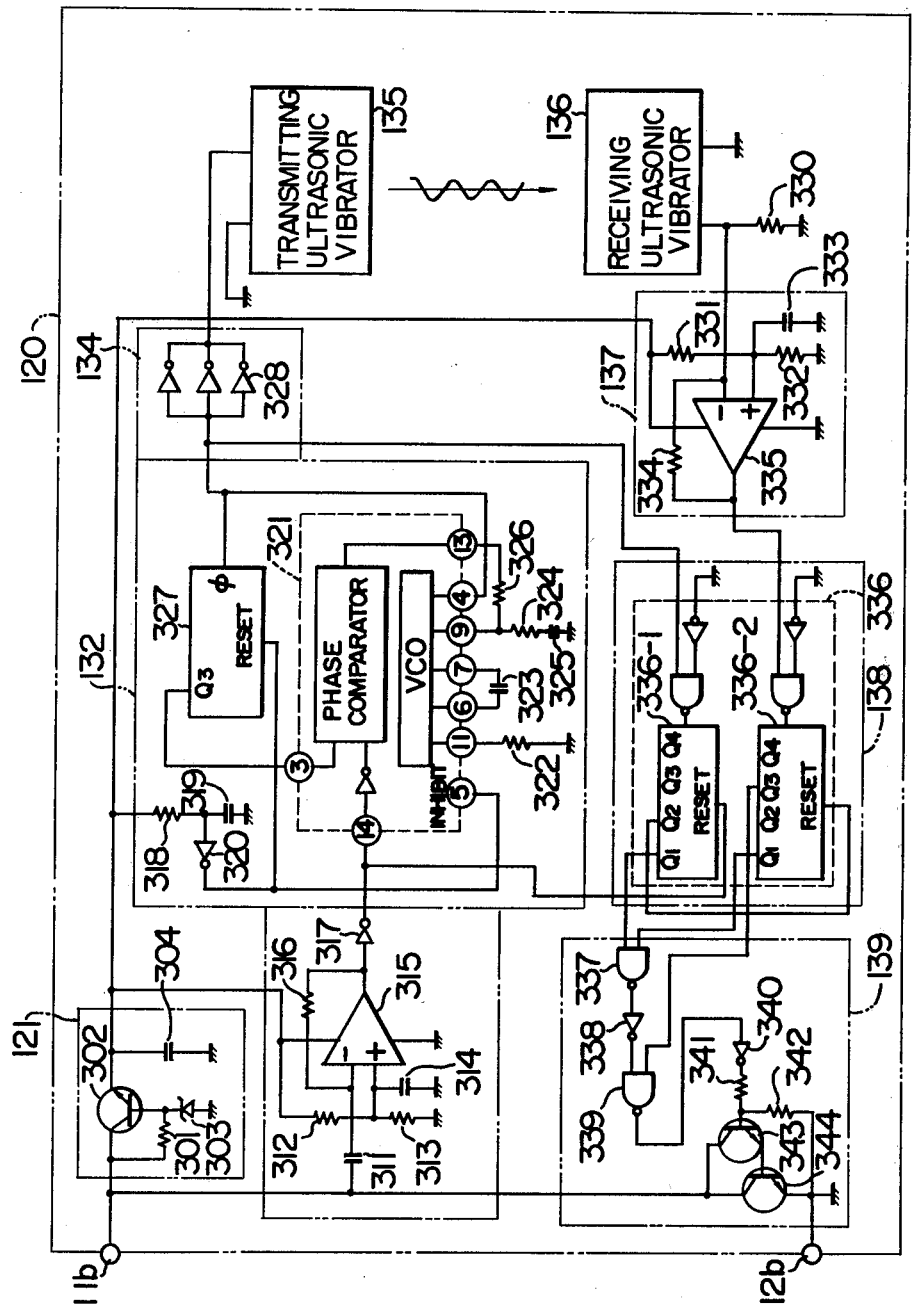
FIG. 3 is a wiring diagram of the sensor section shown in FIG. 1.

Next, the details and operation of the embodiment constructed as described above will be described with reference to FIG. 2 showing a wiring diagram of the display section and FIG. 3 showing a wiring diagram of the sensor section. In the display section 100 of FIG. 2, the high frequency oscillator circuit 101 is a known type of oscillator circuit comprising inverter gates 201 and 202, resistors 204 and 205, capacitors 206 and 207 and a quartz crystal 203. Its oscillation pulse signals are applied to the input of the reference circuit 102 comprising counters 211, 212 and 213 which are arranged so that a signal of 5 KHz or one Nth of the transmitting vibrator exciting frequency (40 KHz in this embodiment) is generated on its output line 214. In this embodiment, the counter 211 comprises the known RCA COS/MOS CD4024 and the counters 212 and 213 each comprises the CD4017, and consequently the voltage waveform shown in (401) of FIG. 4 is generated on the output line 214.

Figure 4:
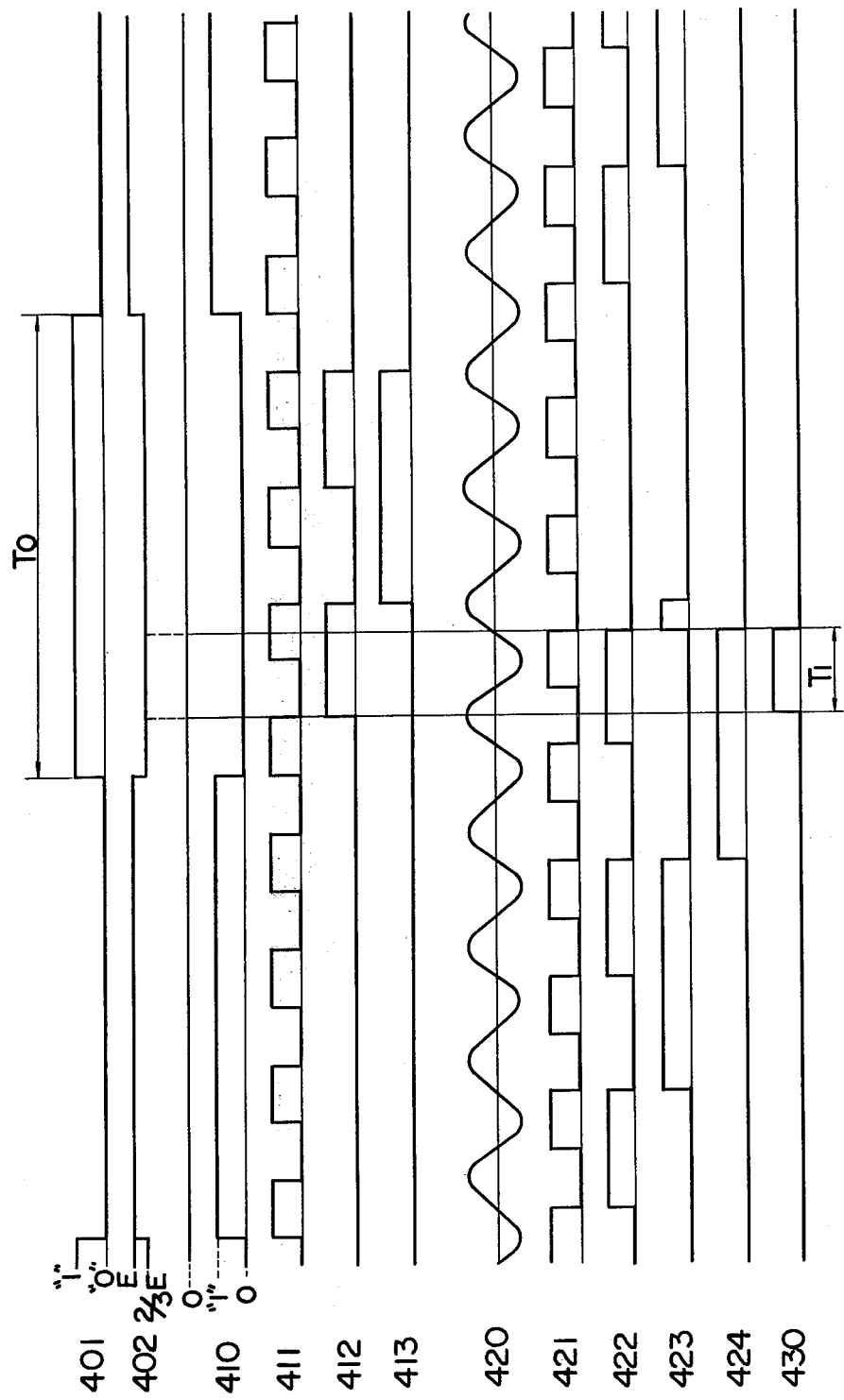
FIGS. 4, 5, 6, 7, 8, 9 and 10 are voltage waveform diagrams useful for explaining the operation of the apparatus of the invention.

The signal 401 of FIG. 4 is applied to the base of a transistor 221 in the input/output circuit 103 and consequently the transistor 221 is turned on during a "1" period $T_0$. Here the ratio between the resistance value of a resistor 223 having one end connected to a power source 13 and that of a resistor 222 having one end connected to the collector of the transistor 221 is selected 1:2. As a result, the voltage waveform shown in (402) of FIG. 4 is generated at a terminal 11a and this voltage waveform has a voltage which is decreased to $\frac{2}{3}$ of the supply voltage of E volts during the period $T_0$ (in this embodiment the power source is the automobile battery and thus the supply voltage is 12 volts). This signal 402 is applied to a sensor section terminal 11b of FIG. 3 and it is then applied to the input of the stabilizing power supply 121 comprising a resistor 301, a transistor 302, a Zener diode 303 and a capacitor 304. A stabilized DC voltage (7 volts in this embodiment) is generated at the output of the stabilizing power supply 121.

The signal 402 is also introduced into the frequency detection circuit 131 comprising capacitors 311 and 314, resistors 312, 313 and 316, an amplifier 315 and an inverter gate 317 end consequently the signal shown in (410) of FIG. 4 and having a frequency which is one Nth of the exciting frequency is generated at the output of the inverter gate 317. The signal 410 is applied to an input terminal 14 of a phase-locked loop circuit 321 in the frequency multiplier circuit 132. The circuit 321 may be comprised of the RCA CD4046. The circuit 321 has its output terminal 4 connected to the input of a counter 327 (e.g., the RCA CD4024) having its Nth stage output (the third-stage output in this embodiment) connected to an input terminal 3 of the phase-locked loop circuit 321. By selecting the values of resistors 322, 324 and 326 and capacitors 323 and 325 of the circuit 321 to suit the frequency used, a voltage waveform is generated at the output terminal 4 of the circuit 321 so as to always maintain the signals at its output terminals 14 and 3 in phase with each other. In other words, in the present embodiment the frequency 5 KHz is fed to the input terminal 14 and the operation is such that the frequency at the output terminal 4 is divided by 8 in the counter 327 and the resulting frequency from its output $Q_3$ or frequency 5 KHz is applied to the input terminal 3 of the phase-locked loop circuit 321. Consequently, an exciting frequency of $5 \times 8 = 40$ (KHz) appears at the output terminal 4. This voltage waveform is shown in (411) of FIG. 4. The signal 411 is fed to the exciting circuit 134 comprising three parallel connected inverters 328 and its output signal always excites the transmitting ultrasonic vibrator 135. The resulting sound wave is always received by the receiving ultrasonic vibrator 136 which in turn generates at its output the sinusoidally varying voltage waveform shown in (420) of FIG. 4. The signal 420 is applied to the amplifier circuit 137 comprising resistors 331, 332 and 334, a capacitor 333 and an amplifier 335 and the amplifier circuit 137 generates at its output the voltage shown in (421) of FIG. 4.

The received signal or signal 421 and the transmitted signal or signal 411 are applied to the phase difference detection circuit 138. The phase difference detection circuit 138 comprises a frequency divider circuit 336 which may be comprised of the RCA CD4520. It will thus be seen that the voltage waveforms shown in (412) and (413) of FIG. 4 are generated respectively at outputs $Q_1$ and $Q_2$ of a frequency divider 336-1 which receives the transmitted signal 411 as its input signal and the voltage waveforms shown in (422), (423) and (424) of FIG. 4 are generated respectively at outputs $Q_1$, $Q_2$ and $Q_3$ of a frequency divider 336-2 which receives the received signal 421 as its input signal. The $Q_1$ outputs of the frequency dividers 336-1 and 336-2 are applied to the inputs of a NAND gate 337 in the output circuit 139 and the output of the NAND gate 337 is inverted by an inverter gate 338, thus generating a phase difference $T_1$ between the transmitted and received signals as shown in (430) of FIG. 4.

Figure 5:
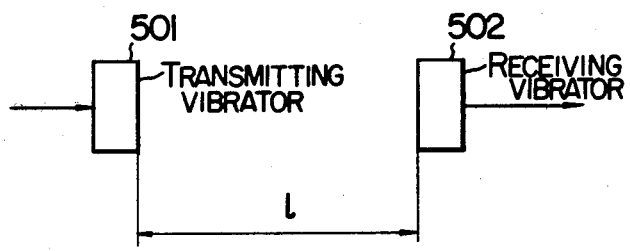
Figure 5:
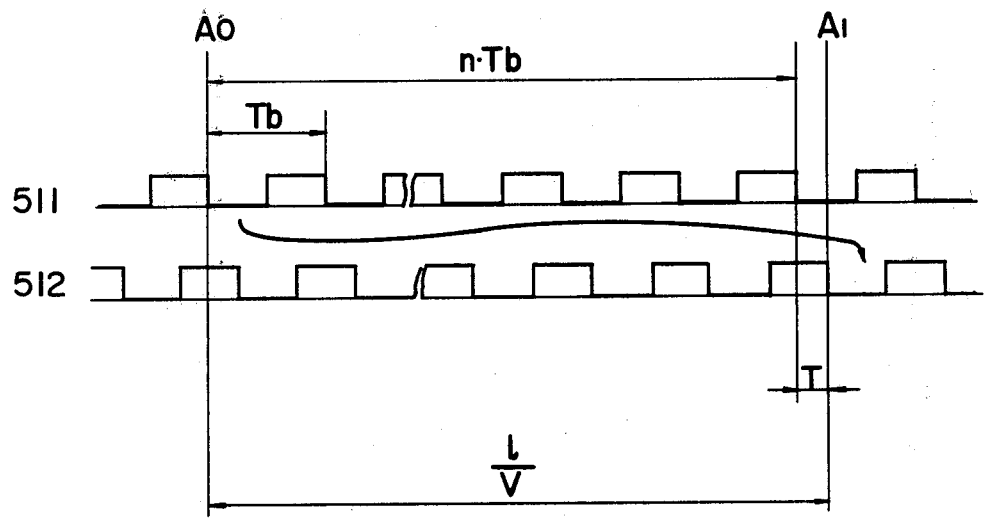

The phase difference $T_1$ will now be described in some greater detail with reference to FIG. 5. In the Figure, assuming that with the distance between a transmitting ultrasonic vibrator 501 and a receiving ultrasonic vibrator 502 being at a fixed value l, if a carrier wave 511 is received at a time $A_0$ and the signal transmitted by the transmitting vibrator 501 is received at a time $A_1$, then the required time t for propagation from the time $A_0$ to $A_1$ is given by $t = l/V$ (V is the velocity of sound). During the time t the transmitting vibrator 501 generates n pulse signals (n=0, 1, 2 ...), and consequently the phase difference T in pulse signal, particularly pulse train between the receiving vibrator 502 and the transmitting vibrator 501 is given by $T = (l/V) - n \cdot T_b$ (where $T_b$ is the period of pulse signals). It will thus be seen from this equation that the width of the phase difference T varies depending on the sound velocity V or the air temperature.

Figure 6:
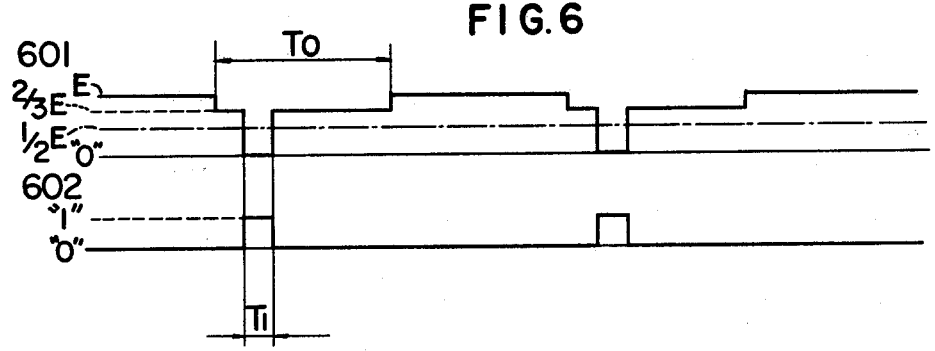
Figure 7:
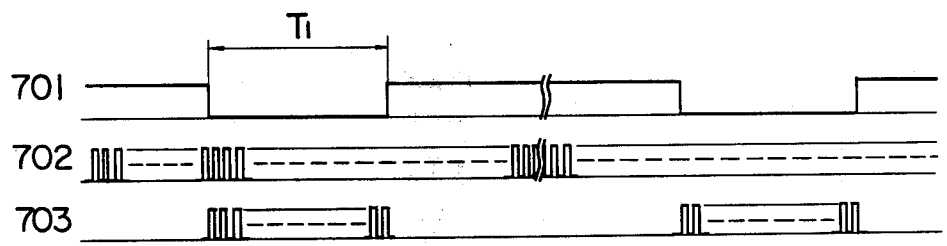

The phase difference signal 430 is then applied to one input of a NAND gate 339 whose other input receives the $Q_3$ output signal 424 of the frequency divider 336-2, thus generating an inverted signal of the signal 430 at the output of the NAND gate 339. The signal 424 is an error prevention signal for ensuring that the phase difference signal 430 is always generated during the time period T of FIG. 4 or during the time that the potential of the signal 402 on the signal line 11 goes to $\frac{2}{3}$E. The output signal of the NAND gate 339 is inverted by an inverter gate 340 and consequently transistors 343 and 344 are turned on only during the time period $T_1$. As a result, the voltage waveform shown in (601) of FIG. 6 is generated at the terminal 11b with its potential going to zero volts during the time period $T_1$. The voltage waveform 601 also appears at the terminal 11a of the display section of FIG. 2 which is connected to the terminal 11b through the signal line 11. Consequently, the signal 601 is fed to an inverter gate 226 of the input/output circuit 103 through its resistosr 224. Since the threshold of the inverter gate 226 is selected ½E, the voltage waveform shown in (602) of FIG. 6 is generated at its output which goes to the "1" level during the time period $T_1$. Consequently, the voltage waveform shown in (701) of FIG. 7 is generated at the output of an inverter gate 227. The signal shown in (701) of FIG. 7 is identical with that shown in (602) of FIG. 6 which was increased in time width and then inverted. The signal 701 modulates a high frequency signal 702 from the reference circuit 102 by a NOR gate 330 and consequently the NOR gate 330 generates at its output a modulated pulse signal 703 having the high frequency pulses superposed thereon during the time period $T_1$. In other words, it will be seen that when the phase difference $T_1$ varies with a change in the air temperature, the number of high frequency pulses generated during the time period $T_1$ is varied correspondingly.

Figure 8:
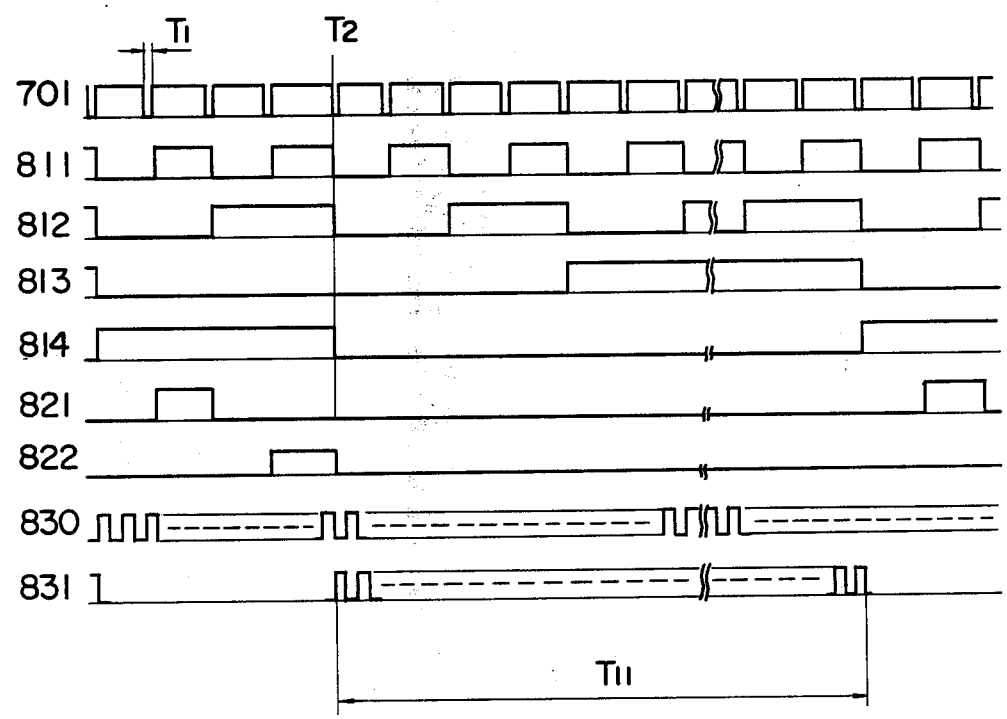

The output signal of the inverter gate 227 which is shown in (701) of FIG. 8 and identical with that shown in (701) of FIG. 7, is applied to a counter 232 of the integrating circuit 104 and the counter 232 counts $2^m$ pulses of the signal 701 ($2^{12}$ pulses in this embodiment) to generate signals during a certain time period. The resulting output signals corresponding to the $2^1$, $2^2$, $2^3$ and $2^m$ pulses are respectively shown in (811), (812), (813) and (814) of FIG. 8. These signals are applied to the logic circuit 105 comprising inverter gates 241, 245, 246 and 247 and NAND gates 242, 243 and 244, so that the storage signal shown in (821) of FIG. 8 is generated at the output of the inverter gate 246 and the reset signal shown in (822) of FIG. 8 is generated at the output of the inverter gate 245. The output of the NAND gate 244 goes to "0" at the instant that the output $Q_3$ of the counter 232 goes to "1" with its output $Q^m$ being at "1" and the counters 232 and 231 are returned to the initial states through the inverter gate 247. The previously mentioned output of the NOR gate 230 or the modulated pulse signal 703 is applied to the input of the counter 231 and consequently the signal shown in (830) of FIG. 8 is generated at an output $Q_{m-1}$ of the counter 231 in response to the counting of $Q_{m-1}$ pulses. Thus, the resulting integrated signal 830 and the $Q_m$ output signal 814 of the counter 232 are applied to a NOR gate 234 which in turn generates at its output the signal shown in (831) of FIG. 8. It should be apparent that the number of pulses generated during the time period $T_{11}$ of FIG. 8 is equal to the average value of the number of pulses generated during the time period $T_1$ of the modulated pulse signal 703. Here the modulated pulse signal 703 is integrated for some time and the average value of the phase differences during this time is produced.

The resulting output signal 831 of the NOR gate 234 is applied to the clock input terminal of an up/down counter 251 of the counter circuit 106 which may for example be a presettable up/down counter (e.g., the RCA CD4510B). The up/down counter 251 generates at its carry-out terminal a signal consisting of a single pulse in response to every 10 pulses applied to the clock terminal. The carry-out output signals are applied to the clock terminal of the following up/down counter 252 so that of the displayed number the up/down counter 251 represents the "ones" digit and that of the up/down counter 251 represents the "tens" digit.

Assume now that the counter 251 has its set inputs $P_1$, $P_2$, $P_3$ and $P_4$ preset altogether to "0" and the counter 252 has its inputs $P_1$, $P_2$ and $P_3$ preset to "0" and $P_4$ preset to "1" as in the present embodiment. In other words, if the preset input is 80, the output changes to 79, 78, 77, . . . in response to each of the pulses applied to the clock terminal of the counter 251. As a result, when the reset signal 822 shown in FIG. 8 is applied to the preset enable terminal of the counters 251 and 252, respectively, the outputs $Q_1$, $Q_2$, $Q_3$ and $Q_4$ of the counter 251 each generates a "1" signal and the outputs $Q_1$, $Q_2$, $Q_3$ and $Q_4$ of the counter 252 each generates a "0" signal except the output $Q_4$ which generates a "1" signal. When the output signal 831 of the NOR gate 234 is applied to the clock terminal of the counter 251, the outputs $Q_1$, $Q_2$, $Q_3$ and $Q_4$ of the counter 251 change as shown in (911), (912), (913) and (914) of FIG. 9 and consequently the outputs $Q_1$, $Q_2$, $Q_3$ and $Q_4$ of the counter 252 change as shown in (921), (922), (923) and (924) of FIG. 9 in response to a signal 920 generated at the carry-out terminal of the counter 251. Assuming now that 55 pulses are generated during the time period $T_{11}$ shown in FIG. 9, the outputs $Q_1$, $Q_2$, $Q_3$ and $Q_4$ of the counter 251 respectively go to "1," "0," "1" and "0" and the outputs $Q_1$, $Q_2$, $Q_3$ and $Q_4$ of the counter 252 respectively go to "0", "1", "0" and "0" so as to indicate the output during the period $B_2$ to $B_3$ or $80-55=25$. These output signals are applied to circuits 253 and 254 for driving the display unit 108 (comprising fluorescent readout tubes in this embodiment). Each of the circuits 253 and 254 may be comprised of the RCA CD4056. The outputs of the counter 252 are applied to the circuit 254 through an inhibit circuit 256 (enclosed by a dotted line) comprising NOR gates and inverter gates so that only when all the outputs of the counter 252 are at "0," that is, when the "tens" digit of the display is zero the signals are inhibited, and only the "ones" digit of the display is indicated.

Figure 9:
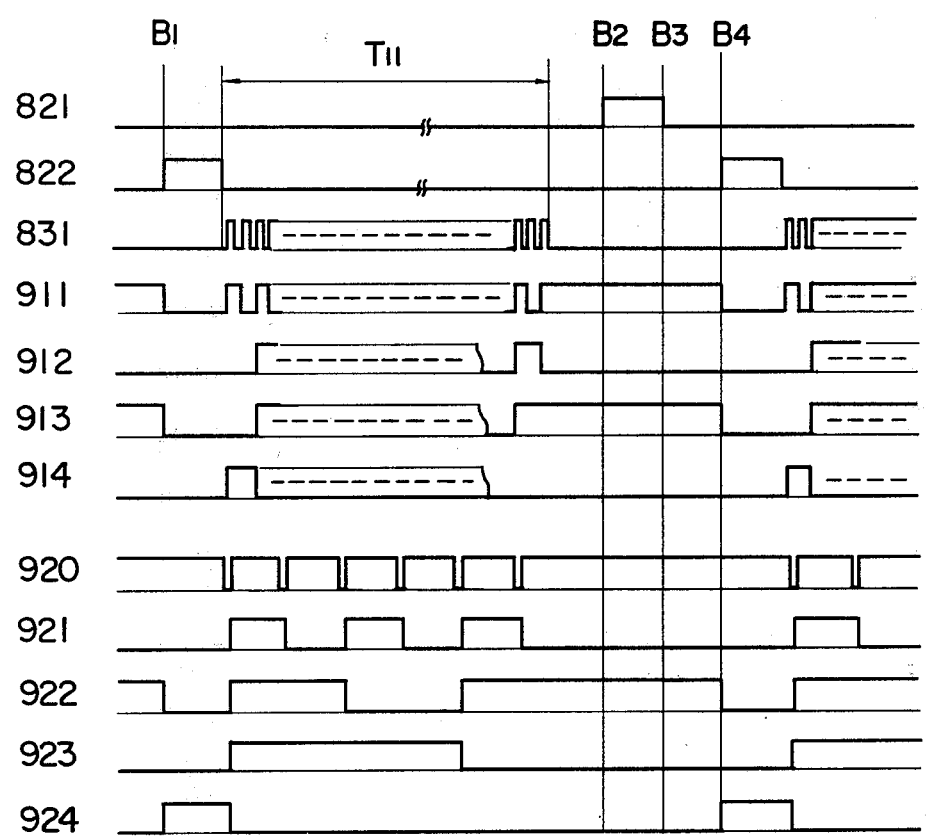

On the other hand, the storage signal shown in (821) of FIG. 9 is applied to the drive circuits 253 and 254, so that when the storage signal goes to "1," the current output states of the counters 251 and 252 are stored and the display unit indicates a number "25," thus indicating the temperature of the medium to be measured or air is 25° C. When a time $B_4$ in FIG. 9 is reached, the counters 251 and 252 are set to the initial states, with the result that the same operation as mentioned previously is effected in response to another input signal 831 and a display corresponding to the outputs of the drive circuits 253 and 254 is made.

Figure 10:
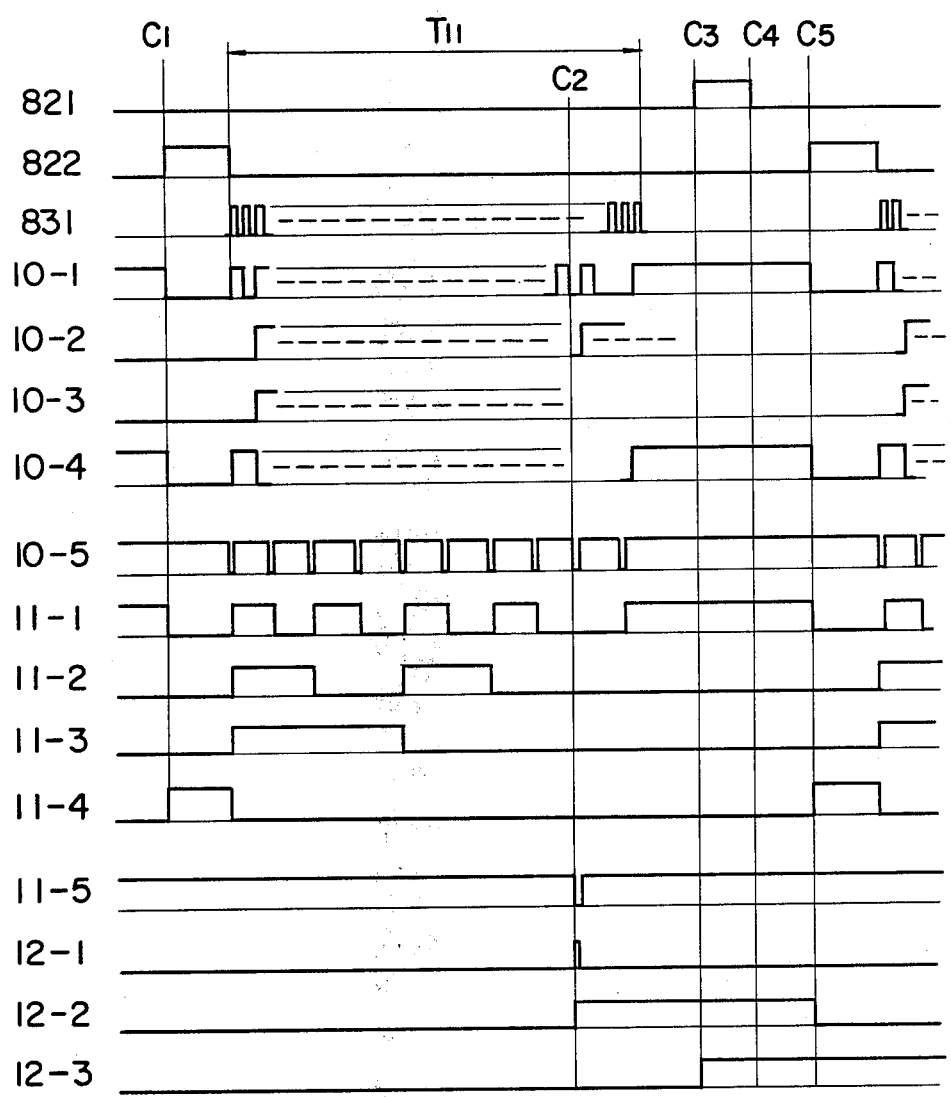

Next, consider a case where the temperature of the medium to be measured or air is decreased to a subzero temperature on the Celsius scale. It will be apparent from the previously mentioned equation $T=(l_0/V)-n\cdot T_b$ that the phase difference $T_1$ of the phase difference detection signal in (701) of FIG. 7 is increased. Assuming now that the number of pulses generated during the time period $T_{11}$ of the signal in (831) of FIG. 10 is 99. In the same manner as mentioned previously, the counters 251 and 252 start to perform down counting at a time $C_1$ in FIG. 10 and thus their outputs change as shown in (10-1), (10-2), (10-3), (10-4) and (10-5) and (11-1), (11-2), (11-3) and (11-4) of FIG. 10. However, when 80 pulses have been applied to the clock terminal of the counter 251 so that $80-80=0$ at a time $C_2$, the outputs of the counters 521 and 252 all go to "0" and the signal shown in (11-5) of FIG. 10 is generated at the carry-out terminal of the counter 252. The signal 11-5 and the output signal 10-5 at the carry-out terminal of the counter 251 are applied to a NOR gate 355 and a signal 12-1 is generated at its output which goes to "1" at the time $C_2$. The signal 12-1 is applied to the clock terminal of a D-type flip-flop 261 in the comparison circuit 107 and consequently the output Q of the D-type flip-flop 261 goes to "1" at the time $C_2$ as shown in (12-2) of FIG. 10. This "1" signal is applied to the up/down terminal of the counters 251 and 252, respectively, and consequently the counters 251 and 252 are set to start counting up at the time $C_2$. Thus, from the time $C_2$ on the output of the counters 251 and 252, respectively, takes the form of a signal which increases in accordance with the number of input pulses. Consequently, during the time interval between times $C_3$ and $C_4$ the outputs change to show $80-99=-19$, that is, the outputs $Q_1$, $Q_2$, $Q_3$ and $Q_4$ of the counter 251 go to "1," "0," "0" and "1," respectively, and the outputs $Q_1$, $Q_2$, $Q_3$ and $Q_4$ of the counter 252 go to "1," "0," "0" and "0," respectively, thus causing the digits 19 to appear on the display.

On the other hand, the signal 12-2 from the output Q of the D-type flip-flop 261 which went to "1" at the time $C_2$ is applied to the D terminal of the following D-type flip-flop 262 and the storage signal 821 is also applied to its clock terminal, thus causing the D-type flip-flop 262 to generate at its output Q a signal 12-3 which goes to "1" at the time $C_3$. The signal 12-3 drives a transistor 264 through an inverter 263 and thus the display unit 108 is caused to display a minus sign. As a result, a display of "$-19$" is provided on the display unit 108 thus indicating that the temperature of the air to be measured is $-19°$ C. In FIG. 2, diodes 291, 296 and 297, resistors 292, 295 and 298, a Zener diode 293 and a capacitor 294 are elements provided to protect or assist the operation of the entire circuitry and they will not be described in any detail.

While, in the embodiment described above, regarding the level of the transmitting ultrasonic vibrator exciting frequency its high level is set to the power supply voltage of E volts and its low level to ⅜E volts and the level of phase difference signal corresponding to air temperature to 0 volt to distinguish them from one another, the invention is not intended to be limited thereto.

Further, while, in the above described embodiment, the display section transmit to the sensor section the frequency which is one Nth (N=8) of the exciting frequency, where the temperature of air or medium does not vary considerably or where the maximum possible pulse width of phase difference detection signal is less than ½ of the exciting frequency pulse width, it is only necessary to transmit the exciting frequency from the display section 100 to the sensor section 120.

We claim:
1. An apparatus for measuring a temperature of an ultrasonic wave propagation medium comprising:
an electric power source for supplying a direct current voltage having a first amplitude;
first pulse means energized by said direct current voltage of said electric power source for producing a train of first pulses at a first fixed frequency;
first amplitude modulation means for modulating said direct current voltage of said electric power source from said first magnitude to a second magnitude in response to said first pulses of said first pulse means, said first amplitude modulation means producing a modulated voltage the amplitude of which changes between said first and second amplitudes at said first fixed frequency;
an electric wire one end of which is connected to said first amplitude modulation means;
voltage regulator means connected to the other end of said electric wire for regulating said modulated voltage supplied from said first amplitude modulation means through said electric wire, said voltage regulator means supplying a regulated voltage;
second pulse means connected to said the other end of said electric wire and energized by said regulated voltage of said voltage regulator means for detecting amplitude changes between said first and second amplitudes of said modulated voltage supplied from said amplitude modulation means through said electric wire, said second pulse means producing a train of second pulses at a frequency equal to said first fixed frequency of said first pulses;
third pulse means energized by said regulated voltage of said voltage regulator means for subjecting said second pulses of said second pulse means to a frequency multiplication, said third pulse means producing a train of third pulses at a third fixed frequency higher than said frequency of said second pulses;
transmitter means for transmitting ultrasonic waves into an ultrasonic wave propagation medium in response to said third pulses of said third pulse means;
receiver means for receiving said ultrasonic waves transmitted from said transmitter means through said porpagation medium, said receiver means producing a train of fourth pulses in response to received ultrasonic waves;
fifth pulse means energized by said regulated voltage of said voltage regulator means for detecting phase differences between said third and fourth pulses produced respectively from said third pulse means and said receiver means, said fifth pulse means producing a train of fifth pulses having respective time intervals equal to detected phase differences;
second amplitude modulation means connected to said the other end of said electric wire for modulating said modulated voltage of said first modulation means from said second amplitude to a third amplitude in response to said fifth pulses;
sixth pulse means connected to said one end of said electric wire for detecting amplitude changes between said second and third amplitudes of said modulated voltage modulated by said second amplitude modulation means, said sixth pulse means producing a train of sixth pulses having time intervals equal to said time intervals of said fifth pulses of said fifth pulse means; and
measuring means energized by said direct current voltage of said electric power source for measuring said time intervals of said sixth pulses of said sixth pulse means, said measuring means producing outputs indicative of a measured time interval.

* * * * *